(12) United States Patent
van Dongen et al.

(10) Patent No.: US 10,874,710 B2
(45) Date of Patent: Dec. 29, 2020

(54) METHODS, REAGENTS AND KITS FOR DETECTING MINIMAL RESIDUAL DISEASE

(71) Applicant: Erasmus University Medical Center Rotterdam, Rotterdam (NL)

(72) Inventors: Jacobus Johannes Maria van Dongen, Rotterdam (NL); José Alberto Orfao de Matos Correia e Vale, Salamanca (ES); Juan Alejandro Flores Montero, Salamanca (ES); Julia Maria Almeida Parra, Salamanca (ES); Vincent Henricus Johannes Van der Velden, Rotterdam (NL); Sebastian Böttcher, Kiel (DE); Anthonie Willem Langerak, Rotterdam (NL); Ester Mejstříková, Prague (CZ); Tomasz Szczepański, Zabrze (PL); Matthias Ritgen, Kiel (DE); Paulo Jorge Monteiro Da Silva Lucio, Lisbon Codex (PT)

(73) Assignee: Erasmus University Medical Center Rotterdam, Rotterdam (NL)

( * ) Notice: Subject to any disclaimer, the term of this patent is extended or adjusted under 35 U.S.C. 154(b) by 364 days.

(21) Appl. No.: 15/812,384

(22) Filed: Nov. 14, 2017

(65) Prior Publication Data
US 2018/0140664 A1 May 24, 2018

Related U.S. Application Data (62) Division of application No. 14/407,268, filed as application No. PCT/NL2013/050420 on Jun. 14, 2013, now abandoned.

(60) Provisional application No. 61/659,524, filed on Jun. 14, 2012.

(51) Int. Cl.
| | |
|---|---|
| A61K 38/16 | (2006.01) |
| G01N 33/574 | (2006.01) |
| A61K 38/17 | (2006.01) |
| A61K 39/02 | (2006.01) |
| A61K 39/09 | (2006.01) |

(52) U.S. Cl.
CPC ........ *A61K 38/164* (2013.01); *A61K 38/1716* (2013.01); *A61K 39/025* (2013.01); *A61K 39/09* (2013.01); *G01N 33/57426* (2013.01); *G01N 33/57484* (2013.01)

(58) Field of Classification Search
CPC ....... G01N 33/57426; G01N 33/57484; G01N 15/14; G01N 2015/1006; A61K 38/164; A61K 38/1716; A61K 39/025; A61K 39/09
See application file for complete search history.

(56) References Cited

U.S. PATENT DOCUMENTS

| | | | |
|---|---|---|---|
| 5,538,855 | A | 7/1996 | Orfao de Matos Correira e Vale |
| 9,880,158 | B2 | 1/2018 | Van Dongen et al. |
| 2004/0224371 | A1 | 11/2004 | De Matos Correia E Valle |
| 2012/0165213 | A1 | 6/2012 | van Dongen et al. |
| 2015/0160226 | A1 | 6/2015 | van Dongen et al. |

FOREIGN PATENT DOCUMENTS

EP   2259065   12/2010

OTHER PUBLICATIONS

Davine Hofste op Bruinink, et al "Flowcytonnetric Minimal Residual Disease Assessment in the EMN-02/HOVON-95 MM Trial: Used Methods and a Comparison of Their Sensitivity" Blood (Dec. 2, 2016) 128 (22): 2072; doi: 10.1182/blood.V128.22.2072.2072. (Year: 2016).*

Van Dongen JJM, et al., "Euroflow Antibody Panels for Standardized N-Dimensional Flow Cytometric Immunophenotyping of Normal, Reactive and Malignant Leukocytes" Leukemia (Sep. 5, 2012 published (online), May 3, 2012 pre-publish draft), 26(9), pp. 1908-1975; doi:10.1038/leu.2012.120; PMID: 22552007. (Year: 2012).*

Flores-Montero J, et al "Next Generation Flow for Highly Sensitive and Standardized Detection of Minimal Residual Disease in Multiple Myeloma" Leukemia Oct. 2017 (Epub Jan. 20, 2017); 31(10), pp. 2094-2103; doi:10.1038/leu.2017.29; PMID: 28104919. (Year: 2017).*

Gorczyca et al., "Subset of T-cell prolymphocytic leukemia expresses CD117: Potential target for therapy" Blood vol. 104 (11): Part 2, pp. 2188, Nov. 16, 2004, Abstract.

Kraan et al., "Flow cytometric immunophenotyping of cerebrospinal fluid", Current Protocols in Cytometry, Jul. 1, 2008, vol. 45, pp. 6.25.1-6.25.16.

Nieto et al., "Increased frequency (12%) of circulating chronic lymphocytic leukemia-like B-cell clones in healthy subjects using a highly sensitive multicolor flow cytometry approach" Blood, vol. 114, No. 1; pp. 33-37; published online May 6, 2009.

Rawston et al., "Flow cytometric protein expression profiling as a systematic approach for developing disease-specific assays: identification of a chronic lymphocytic leukaemia-specific assay for use in rituximab-containing regimens" Leukemia, vol. 20, pp. 2102-2110, 2006.

(Continued)

*Primary Examiner* — Aaron J Kosar
(74) *Attorney, Agent, or Firm* — Dentons US LLP (57) ABSTRACT

The invention relates to the field of minimal residual disease (MRD) diagnostics, which is progressively more applied for the evaluation of treatment effectiveness in patients with a hematological malignancy, such as B-cell precursor acute lymphoblastic leukemia (BCP-ALL), B-cell chronic lymphocytic leukemia (B-CLL), and multiple myeloma (MM). Provided are unique reagent compositions with carefully selected and thoroughly tested combinations of antibodies, for ≥8-color flow cytometric stainings as well as for 10-color and 12-color flow cyometric stainings, which can reach sensitivities of at least $10^{-4}$, even down to $10^{-5}$. Also provided are diagnostic kits and methods for detecting MRD.

9 Claims, 6 Drawing Sheets

(56) References Cited

OTHER PUBLICATIONS

Brunetti et al., "CD200/OX2, a cell surface molecule with immunoregulatory function, is consistently expressed on hairy cell leukaemia neoplastic cells" British J Haematol. Jun. 2009; 145(5): pp. 665-667.

Martins et al., "Quantification and Immunophenotypic Characterization of Bone Marrow and Umbilical Cord Blood Mesenchymal Stem Cells by Multicolor Flow Cytometry", Transplant Proc. Apr. 2009; 41(3); pp. 943-946.

BD Biosciences. BD PAC-H7 Conjugated Antibody Reagents, 2008.

Berhanu et al., "Optimized lymphocyte isolation methods for analysis of chemokine receptor expression" J Immunological Methods, vol. 279, No. 1-2, Aug. 2003, pp. 199-207.

Abrams et al., "3-Carboxy-6-chloro-7-hydroxycoumarin: a highly fluorescent, water-soluble violet-excitable dye for cell analysis", Analytical Biochemistry, Mar. 15, 2009, vol. 386, No. 2, pp. 262-269.

Anonymus, "Consensual European Immunophenotyping Panels for Leukemia", 6th PCRDT, https://www.leukemia-net.org/content/diagnostics/diagnostics/documents/e5821/infoboxContent5822/WP10consensual_panels.pdf retrieved from the internet Apr. 16, 2017, 14 pages.

Boettcher et al., "Improved differential diagnosis between whodefined mature B-cell malignancies using integrated 8-color flow cytometry and novel software for multivariate analysis of immunophenotypic data", Haematologica—The Hematology Journal, vol. 94, No. Suppl. 2, Jun. 2009, pp. 276.

Boulassel et al., "Immunophenotypic patterns of CD8<+> T cell subsets expressing CD8alphaalpha and IL-7Ralpha in HIV-1-infected subjects", Clinical Immunology, vol. 124, No. 2, Jul. 18, 2007, pp. 149-157.

Campana et al., "Immunophenotyping of leukemia", Journal of Immunological Methods, vol. 243, No. 1-2, Sep. 21, 2000, pp. 59-75.

Lhermitte et al., "A single 8-color flow-cytometric immunostaining allows delineation of both typical myeloid and lymphoid acute leukemia and undifferentiated/immature acute leukemia (on behalf of the Euroflow Consortium", Haematologica—The Hematology Journal, vol. 94, No. Suppl. 2, Jun. 2009, pp. 110-111, and 14th Annual Meeting of the European-Hematology-Association; Berlin, Germany, Jun. 4-7, 2009.

Lhermitte et al., "A single 8-color flow-cytometric immunostaining allows delineation of both typical myeloid and lymphoid acute leukemia and undifferenciated/immature acute leukemia ", Jun. 4, 2009, retrieved from the internet: hllp://www.euroftow.org/imagenes/publications/lhermitte,_alot_poster,_eha_2009,_berlin.pdf, retrieved Nov. 17, 2009.

Rawstron et al., "Selection of Markers for Identification of Disease-Specific Phenotypes for Diagnosis and Monitoring of B-Lymphoproliferative Disorders by Flow Cytometry", Haematologica—The Hematology Journal, vol. 94, No. Suppl. 2, Jun. 2009, pp. 275-276.

Vaickus et al., "Immune Markers in Hematologic Malignancies", Critical Reviews in Oncology/Hematology, vol. 11. No. 4, Dec. 1, 1991, pp. 267-297.

International Search Report from PCT Application No. PCT/NL2010/050332, dated Oct. 14, 2010, 9 pages.

Notification Concerning Transmittal International Preliminary report on Patentability and Written Opinion from PCT Application No. PCT/NL2010/050332, dated Dec. 6, 2011, 12 pages.

Drach et al., "Flow cytometric detection of cytoplasmic antigens in acute leukemias: implications for lineage assignment", Leukemia Research, New York, 17(5):455-461 (1993).

Haferlach et al., "Modern diagnostics in acute leukemias", Critical Reviews in Oncology/Hematology, Elsevier, Amsterdam, 56(2):223-234 (2005).

European Search Report dated Sep. 16, 2016 in European Patent Application No. 16166647.4, filed Jun. 14, 2013.

Konoplev, et al., "Immunophenotypic Profile of Plasma Cells as Assessed by Multi-Color Flow Cytometry: A Comparison between Lymphoplasmacytic Lymphoma and CD45 Positive Myeloma," Modern Pathology, Nature Publishing Group, Feb. 1, 2012, pp. 348A, vol. 25, No. Suppl. 2, Great Britain.

Cannizzo, et al., "The Role of CD19 and CD27 in the Diagnosis of Multiple Myeloma by Flow Cytometry," American Journal of Clinical Pathology, Mar. 1, 2012, pp. 377-386, vol. 137, No. 3, United States.

Ng, et al., "Assessing Minimal Disease in Plasma Cell Neoplasms: A Comparison between Multicolor Flow Cytometry and Immunohistochemistry," Modern Pathology, Nature Publishing Group, Feb. 1, 2012, pp. 357A, vol. 25, No. Suppl. 2, Great Britain.

Kartsios, et al. "Utility of CD81 Flow Cytometry (FC) Assessment in Diagnostic Evaluation of Plasma Cell (PC) Disorders," Blood, American Society of Hematology, Nov. 1, 2010, pp. 1240-1241, vol. 116, No. 21, United States.

Zhang, et al., "Detection of Minimal Residual Disease of Plasma Cell Myeloma by Five Color Flow Cytometric Immunophenotype Analysis," Blood, American Society of Hematology, Nov. 1, 2010, pp. 793, vol. 116, No. 21, United States.

Wuilleme, et al. "A Single-Tube Seven-Colour Flow Cytometry Assay for Detection of Minimal Residual Disease in Myeloma," Blood, American Society of Hematology, Nov. 1, 2010, pp. 708, vol. 116, No. 21, United States.

International Search Report from corresponding PCT Application No. PCT/NL2013/50420 dated Mar. 11, 2014.

Lucio et al., "Flow Cytometric Analysis of Normal B Cell Differentiation: A Frame of Reference for the Detection of Minimal Residual Disease in Precursor-B-All," Leukemia, 13:419-427 (1999).

Braylan et al., "Optimal Number or Reagents Required to Evaluate Hermatolymphoid Neoplasis: Results of an International Consensus Meeting," Cytometry, 46:23-27 (2001).

Owaidah et al., "Expression of CD66c and CD25 in Acute Lymphoblastic Leukemia as a Predictor of the Presence of BCR/ABL Rearrangement," Hematology Oncology and Stem Cell Therapy, 1:34-37 (2008).

Popov et al., "Immunological Shift on Day 15 of Remission Induction in Children with CD10-Positive B-Cell Precursor ALL Treated by ALL-MB 2008 Protocol," Blood, 114:1-2 (2009).

Van Dongen et al., "Euroflow Antibody Panels for Standardized N-Dimensional Flow Cytometric Immunophentyping of Normal, Reactive and Malignant Leukocytes," Euroflow Antibody Panels Handout at 14th EHA Congress, Berlin, Germany, Jun. 4, 2009, Retrieved from Euroflow.org, URL:http://www.euroflow.org/imagenes/news/euroflow_handout_on_antibody_panels.pdf on Nov. 17, 2009, pp. 1-18.

\* cited by examiner

Figure 1

Panel A

Panel B

Panel C

Panel D

METHODS, REAGENTS AND KITS FOR DETECTING MINIMAL RESIDUAL DISEASE

RELATED APPLICATIONS

This application is a divisional of U.S. patent application Ser. No. 14/407,268, filed Dec. 11, 2014, which is the U.S. National Stage of International Application No. PCT/NL2013/050420, filed Jun. 14, 2013, published in English, which claims the benefit of U.S. Provisional Application No. 61/659,524, filed on Jun. 14, 2012, the entire teachings of the above applications are incorporated herein by reference.

The invention relates to the field of cancer diagnosis, more specifically to means and method for the monitoring of disease development during and after treatment or for the detection of minimal disseminated disease. Cytostatic or cytotoxic treatment induces remission in the majority of patients with lymphoid malignancies. Nevertheless many of these patients relapse. Apparently the current cytostatic or cytotoxic treatment protocols are not capable of killing all malignant cells in these relapsing patients, although they reached so-called complete remission according to cytomorphological criteria. Since the detection limit of cytomorphological techniques is not lower than 1-5% malignant cells, it is obvious that such techniques can only provide superficial information about the effectiveness of treatment, up to $10^{10}$ tumor cells still potentially remaining in the body Techniques with a higher sensitivity to detect "minimal residual disease" or minimal disease (MRD) are needed to obtain better insight in the reduction of tumor mass during induction treatment and further eradication of the malignant cells during maintenance treatment from one or more than one tissue. The application of flow cytometry for detection of MRD is traditionally based on discrimination between malignant cells and normal leukocytes via malignancy-associated phenotypic characteristics, such as aberrant expression, overexpression, and cross-lineage expression of antigens.

Current 4-color and 6-color flow cytometry reaches a fair sensitivity of $10^{-3}$ (to $10^{-4}$) in most patients with a hematological malignancy. However, it should be noted that the detection of low frequencies of malignant cells in blood, bone marrow and other body fluids such as cerebrospinal fluid during and after therapy and after hematopoietic stem cell transplantation can be hampered by high frequencies of normal regenerating cells. The extent and the pattern of regeneration differs per treatment protocol, per phase of treatment, per time of sampling, and seems to be dependent on the intensity of the preceding treatment: the more intensive the treatment, the more prominent the regeneration of hematopoietic cells.

Logically, both the background of regenerating cells and the drug-induced immunophenotypic shifts reduce the sensitivity and specificity of the existing 4-color and 6-color flow cytometric MRD methods. This has mainly lead to approaches in which either multiple combinations of markers are used to evaluate MRD in a patient or, alternatively to use one or a few patient-specific combinations of markers. Recognizing the need for improved diagnostic methods for MRD, the present inventors set out to identify additional markers which could be used to obtain a more sensitive and reliable assay for detecting MRD, particularly based on a fully integrated approach, in which information of multiple markers is combined via multivariate analysis. In addition, this new approach is not anymore limited to individual patients, but is applicable to every patient of a specific disease category, such B-cell precursor acute lymphoblastic leukemia (BCP-ALL), B-cell chronic lymphocytic leukemia (B-CLL) and multiple myeloma (MM).

After careful selection of the relevant markers, design of appropriate combinations of antibodies in multi-color tubes, and the selection of suited fluorochromes (based on need for brightness, compensation, stability, etc.), a set of antibody reagents was developed. The studies were complemented with extensive multicentric evaluation of the consensus panels in order to reshape and achieve an optimal efficiency. The inventors designed novel ≥8-color stainings with carefully selected and thoroughly tested combinations of antibodies, which can reach sensitivities of $10^{-4}$ to $10^{-5}$ Based on design-testing-redesign-retesting-redesign (etc.), specific combinations of fluorochrome-conjugated antibodies have been developed per disease category, such as BCP-ALL, B-CLL and MM. One or two ≥8-color combinations per patient will allow careful MRD monitoring with sensitivities of at least $10^{-4}$. The provided 10-color and 12-color antibody combinations can even better discriminate between normal cells and their malignant counterparts, thereby allowing for MRD detection with sensitivities down to $10^{-5}$.

Here we present novel 8-color 10-color and 12-color antibody combinations for detection of MRD in a sample, e.g. blood or bone marrow, isolated from patients with:
- B-cell precursor acute lymphoblastic leukemia (BCP-ALL)
- B-cell chronic lymphocytic leukemia (B-CLL) or
- Multiple myeloma (MM) and related plasma cell disorders (PCD).

These multi-color immunostainings can be performed according to the so-called EuroFlow protocols as described by Van Dongen et al. Leukemia 2012; 26: 1908-1075 and by Kalina et al. Leukemia 2012; 26: 1986-2010.

Accordingly, the invention provides unique reagent compositions for flow cytometric detection of MRD, comprising a combination of at least eight distinct fluorochrome-conjugated antibodies. In particular, the reagent compositions are of use for detecting MRD in patients with BCP-ALL, B-CLL or MM/PCD. In a preferred embodiment, the composition comprises monoclonal antibodies against a given CD antigen. CD stands for cluster designation and is a nomenclature for the identification of specific cell surface antigens or intracellular antigens defined by monoclonal antibodies. (Monoclonal) antibodies against the indicated markers can be commercially obtained from various companies, including Becton/Dickinson (BD) Biosciences, Dako, Beckman Coulter, CYTOGNOS, Caltag, Pharmingen, Exbio, Sanquin, Invitrogen, and the like.

Flow Cytometric MRD Detection in BCP-ALL

In one embodiment, the invention provides a reagent composition for flow cytometric detection of BCP-ALL cells in a human subject, comprising a panel of at least eight distinct fluorochrome-conjugated antibodies. The BCP-ALL panel comprises antibodies against the four "core markers" CD10, CD19, CD20, CD34 and CD45. Preferably, the panel further comprises one or more antibodies selected from the group of antibodies against CD38, CD81, CyIgμ, and deoxynucleotidyl transferase (NuTdT). Very good results are obtained if the panel further comprises one or more sets of antibodies selected from (a) set of antibodies against CD66c and CD123; (b) set of antibodies against CD304 and CD73; and (c) set of antibodies against SmIgκ and SmIgλ, wherein the antibodies within each set are conjugated to the same fluorochrome. In a specific aspect, the BCP-ALL panel comprises antibodies against CD10, CD19, CD20, CD34, CD45, one or more antibodies selected from the group of antibodies against CD38, CD81, CyIgμ, NuTdT, and two or more sets of antibodies selected from (a) set of antibodies against CD66c and CD123; (b) set of antibodies against CD304 and CD73; and (c) set of antibodies against SmIgκ and SmIgλ, wherein the antibodies within each set are conjugated to the same fluorochrome. For example, a reagent composition comprises distinct fluorochrome-conjugated antibodies directed against one of the following combinations of markers:

(i) CD20, CD45, CD81, CD66c, CD123, CD34, CD19, CD10 and CD38, wherein the antibodies against CD66c and CD123 are conjugated to the same fluorochrome;

(ii) CD20, CD45, CD81, CD304, CD73, CD34, CD19, CD10 and CD38, wherein the antibodies against CD304 and CD73 are conjugated to the same fluorochrome;

(iii) CD20, CD45, NuTdT, SmIgκ, SmIgλ, CyIgµ, CD19, CD34 and CD10, wherein the antibodies against SmIgκ and SmIgλ are conjugated to the same fluorochrome. See for instance the 8-color BCP-ALL MRD Panel 1A.

As another example, it comprises distinct fluorochrome-conjugated antibodies directed against the markers CD20, CD45, CD81, NuTdT, CD34, CD19, CD10 and CD38, and one or more sets of antibodies selected from (a) set of antibodies against CD66c and CD123; (b) set of antibodies against CD304 and CD73; and (c) set of antibodies against SmIgκ and SmIgλ, wherein the antibodies within each set are conjugated to the same fluorochrome. See for instance the 10-color tube in Panel 1B comprising antibodies against the markers CD20, CD45, CD81, NuTdT, CD66c, CD123, CD304, CD73, CD34, CD19, CD10 and CD38.

In a further specific aspect, the composition comprises a combination of fluorochrome-conjugated antibodies directed against the markers CD20, CD45, CD81, NuTdT, CD66c, CD123, CD304, CD73, SmIgκ, SmIgλ, CyIgµ, CD34, CD19, CD10 and CD38, wherein the antibodies against each of the sets CD66c/CD123, CD304/CD73 and SmIgκ/SmIgλ are conjugated to the same fluorochrome. See for instance the 12-color tube in panel 1C.

Suitable fluorochromes for conjugating antibodies for use in the present invention against the recited markers are known in the art. As will be understood, the fluorochromes used within a reagent composition should be distinguishable from each other by flow cytometry. The fluorochromes are preferably selected for brightness, limited spectral overlap and limited need for compensation, stability, etc (see: Kalina et al. Leukemia 2012: 26: 1986-2010).

The following panel of fluorochromes is of particular use in a BCP-ALL reagent composition according to the invention: (1) pacific blue (PacB), brilliant violet 421 (BV421) or Horizon V450, (2) pacific orange (PacO), Horizon V500 (HV500), BV510, Khrome orange (KO) or OC515, (3) fluorescein isothiocyanate (FITC) or Alexa488, (4) phycoerythrin (PE), (5) peridinin chlorphyl protein/cyanine 5.5 (PerCP-Cy5.5), PerCP or PE-TexasRed, (6) phycoerythrin/cyanine7 (PE-Cy7), (7) allophycocyanine (APC) or Alexa647, and (8) allophycocyanine/hilite 7 (APC-H7), APC-Cy7, Alexa680, APC-A750, APC-C750 or Alexa700. After multiple testing rounds, the present inventors observed that very good results can be obtained if the following fluorochromes are chosen: Pacific Blue, brilliant violet 421 or Horizon V450, PacO or Horizon V500, FITC, PE, PerCP-Cy5.5, PE-Cy7, APC, and APC-H7 or APC-A750 or APC-C750. In a specific aspect, the invention provides for a reagent composition shown in Table 1, panel 1A, panel 1B or panel 1C.

TABLE 1

Exemplary reagent compositions for MRD detection in BCP-ALL . . .

Panel 1A. Marker Composition of 8-color BCP-ALL MRD panels of the invention

| tube | PacB | PacO | FITC | PE | PerCPCy5.5 | PECy7 | APC | APCC750 |
|---|---|---|---|---|---|---|---|---|
| 1 | CD20 | CD45 | CD81 | CD66c and CD123 | CD34 | CD19 | CD10 | CD38 |
| 2 | CD20 | CD45 | CD81 | CD304 and CD73 | CD34 | CD19 | CD10 | CD38 |
| 2 | CD20 | CD45 | NuTdT | SmIgκ and SmIgλ | CyIgµ | CD19 | CD34 | CD10 |

Panel 1B. Marker Composition of 10-color BCP-ALL MRD panel of the invention

| F1 | F2 | F3 | F4 | F5 | F6 | F7 | F8 | F9 | F10 |
|---|---|---|---|---|---|---|---|---|---|
| CD20 | CD45 | CD81 | NuTdT | CD66c and CD123 | CD304 and CD73 | CD34 | CD19 | CD10 | CD38 |

Panel 1C. Marker Composition of 12-color BCP-ALL MRD panel of the invention

| F1 | F2 | F3 | F4 | F5 | F6 | F7 | F8 | F9 | F10 | F11 | F12 |
|---|---|---|---|---|---|---|---|---|---|---|---|
| CD20 | CD45 | CD81 | NuTdT | CD66c and CD123 | CD304 and CD73 | SmIgκ and SmIgλ | CyIgµ | CD34 | CD19 | CD10 | CD38 |

Flow Cytometric MRD Detection in B-CLL

In another embodiment, the invention provides a reagent composition for flow cytometric detection of B-cell chronic lymphocytic leukemia (B-CLL) in a human subject, comprising a panel of at least eight distinct fluorochrome-conjugated antibodies, the panel comprising at least antibodies against the seven "core markers" CD5, CD27, CD79b, CD3, CD200, CD81 and CD19. It was found that CD22 and/or Receptor tyrosine kinase-like orphan receptor 1 (ROR1) can be used as valuable additional marker(s). Very good results were obtained in combination with the markers CD43 and CD38.

Preferred marker combinations for detecting B-CLL are as follows:
(a) CD27, CD3, CD79b, CD5, CD22, CD19, CD200 and CD81
(b) CD5, CD3, CD79b, ROR1, CD27, CD19, CD200 and CD81
(c) CD27, CD3, CD79b, ROR1, CD5, CD22, CD19, CD20, CD200 and CD81
(d) CD27, CD3, CD79b, ROR1, CD5, CD22, CD19, CD20, CD200, CD43, CD81 and CD38.

The following panel of fluorochromes is of particular use in a CLL reagent composition according to the invention: (1) pacific blue (PacB), brilliant violet 421 (BV421) or Horizon V450, (2) pacific orange (PacO), Horizon V500 (HV500), BV510, Khrome orange (KO) or OC515, (3) fluorescein isothiocyanate (FITC) or Alexa488, (4) phycoerythrin (PE), (5) peridinin chlorophyl protein/cyanine 5.5 (PerCP-Cy5.5), PerCP or PE-TexasRed, (6) phycoerythrin/cyanine7 (PE-Cy7), (7) allophycocyanine (APC) or Alexa647, and (8) allophycocyanine/hilite 7 (APC-H7), APC-Cy7, Alexa680, APC-A750, APC-C750 or Alexa700. After multiple testing rounds, the present inventors observed that very good results can be obtained if the following fluorochromes are chosen: Pacific Blue, brilliant violet 421 or Horizon V450, PacO or Horizon V500, FITC, PE, PerCP-Cy5.5, PE-Cy7, APC, and APC-H7 or APC-A750 or APC-C750.

In a specific aspect, the invention provides for a reagent composition shown in Table 2.

For example, provided is a reagent composition for flow cytometric detection of MM or PCD in a human subject, comprising a panel of at least eight distinct fluorochrome-conjugated antibodies, the panel comprising at least antibodies against the core markers CD138, CD38, CD56 and CD19, supplemented with at least four additional markers selected from the group consisting of CD27, CD117, CD81, CD229, CD45, CyIgκ and CyIgλ. Preferably, CD45 is the fifth marker, more preferably in combination with the markers CD27, CD117 and CD81, or in combination with the markers CD229, CyIgκ and CyIgλ. Preferred reagent compositions comprise distinct fluorochrome-conjugated antibodies directed against one of the following combinations of markers:
(iv) CD45, CD138, CD38, CD56, CD27, CD19, CD117 and CD81
(v) CD45, CD138, CD38, CD56, CD229, CD19, CyIgκ and CyIgλ
(vi) CD138, CD27, CD38, CD56, CD45, CD19, CD117 and CD81
(vii) CD138, CD27, CD38, CD56, CD229, CD19, CyIgκ and CyIgλ
(viii) CD138, CD27, CD38, CD56, CD45, CD19, CyIgκ and CyIgλ

See for instance the 8-color PCD MRD Panel 3A.

Very good results were obtained using fluorochrome-conjugated antibodies directed against the markers CD138, CD27, CD38, CD56, CD45, CD19, CD117, CD81 and one

TABLE 2

Exemplary reagent compositions for MRD detection in B-CLL

Panel 2A. Composition of 8-color CLL MRD panel

| BV421 | BV510 | FITC | PE | PerCPCy5.5 | PECy7 | APC | APCC750 |
|---|---|---|---|---|---|---|---|
| CD27 | CD3 | CD79b | CD5 | CD22 | CD19 | CD200 | CD81 |
| CD5 | CD3 | CD79b | ROR1 | CD27 | CD19 | CD200 | CD81 |

Panel 2B. Composition of 10-color CLL MRD tube

| F1 | F2 | F3 | F4 | F5 | F6 | F7 | F8 | F9 | F10 |
|---|---|---|---|---|---|---|---|---|---|
| CD27 | CD3 | CD79b | ROR1 | CD5 | CD22 | CD19 | CD20 | CD200 | CD81 |

Panel 2C. Composition of 12-color CLL MRD tube

| F1 | F2 | F3 | F4 | F5 | F6 | F7 | F8 | F9 | F10 | F11 | F12 |
|---|---|---|---|---|---|---|---|---|---|---|---|
| CD27 | CD3 | CD79b | ROR1 | CD5 | CD22 | CD19 | CD20 | CD200 | CD43 | CD81 | CD38 |

Flow Cytometric MRD Detection in Multiple Myeloma/Plasma Cell Disease (MM/PCD)

A still further aspect of the invention relates to a reagent composition for detecting MM or PCD cells. The panel comprises antibodies against the four "core markers" CD138, CD38, CD56 and CD19, supplemented with at least four additional markers selected from the group consisting of CD27, CD117, CD81, CD229, CD45, CyIgκ and CyIgλ. CD45 is a preferred fifth marker, preferably in combination with CD27, CD117 and CD81 or CD229, CyIgκ and CyIgλ.

Provided is a reagent composition with distinct fluorochrome-conjugated antibodies against either one of the following panels of markers:
(n) CD45 CD138 CD38 CD56 CD27 CD19 CD117 CD81
(o) CD45 CD138 CD38 CD56 CD229 CD19 CyIgκ CyIgλ
(p) CD138 CD27 CD38 CD56 CD45 CD19 CD117 CD81
(q) CD138 CD27 CD38 CD56 CD229 CD19 CyIgκ CyIgλ
(r) CD138 CD 27 CD38 CD56 CD45 CD19 CyIgκ CyIgλ or both set(s) of antibodies selected from (a) set of antibodies against CD229 and CD28; and (b) set of antibodies against CyIgκ and CyIgλ. See for instance the 10-color tube in Panel 3B and the 12-color tube in Panel 3C.

The following panel of fluorochromes is of particular use in a MM/PCD reagent composition according to the invention: (1) pacific blue (PacB), brilliant violet 421 (BV421) or Horizon V450, (2) pacific orange (PacO), Horizon V500 (HV500), BV510, Khrome orange (KO) or OC515, (3) fluorescein isothiocyanate (FITC) or Alexa488, (4) phycoerythrin (PE), (5) peridinin chlorophyl protein/cyanine 5.5 (PerCP-Cy5.5), PerCP or PE-TexasRed, (6) phycoerythrin/cyanine7 (PE-Cy7), (7) allophycocyanine (APC) or Alexa647, and (8) allophycocyanine/hilite 7 (APC-H7), APC-Cy7, Alexa680, APC-A750, APC-C750 or Alexa700. After multiple testing rounds, the present inventors observed that very good results can be obtained if the following fluorochromes are chosen: Pacific Blue, brilliant violet 421 or Horizon V450, PacO or Horizon V500, FITC, PE, PerCP-Cy5.5, PE-Cy7, APC, and APC-H7 or APC-A750 or APC-C750.

TABLE 3

Exemplary reagent compositions for MRD detection in MM/PCD

Panel 3A. Composition of PCD MRD panel

| Tube | PacB or BV421 or HV450 | HV500 or PacO | FITC | PE | PerCPCy5.5 | PECy7 | APC | APCH7 or APCA750 or APCC750 |
|---|---|---|---|---|---|---|---|---|
| 1 | CD45 | CD138 | CD38 | CD56 | CD27 | CD19 | CD117 | CD81 |
| 2 | CD45 | CD138 | CD38 | CD56 | CD229 | CD19 | CyIgκ | CyIgλ |
| 3 | CD138 | CD27 | CD38 | CD56 | CD45 | CD19 | CD117 | CD81 |
| 4 | CD138 | CD27 | CD38 | CD56 | CD229 | CD19 | CyIgκ | CyTgλ |
| 5 | CD138 | CD27 | CD38 | CD56 | CD45 | CD19 | CyIgκ | CyIgλ |

Panel 3B. Composition of 10-color PCD MRD panel

| F1 | F2 | F3 | F4 | F5 | F6 | F7 | F8 | F9 | F10 |
|---|---|---|---|---|---|---|---|---|---|
| CD138 | CD27 | CD38 | CD56 | CD45 | CD19 | CD117 | CD81 | CD229 | CD28 |
| CD138 | CD27 | CD38 | CD56 | CD45 | CD19 | CD117 | CD81 | CyIgκ | CyIgλ |

Panel 3C. Composition of 12-color PCD MRD tube

| F1 | F2 | F3 | F4 | F5 | F6 | F7 | F8 | F9 | F10 | F11 | F12 |
|---|---|---|---|---|---|---|---|---|---|---|---|
| CD138 | CD27 | CD38 | CD56 | CD45 | CD19 | CD117 | CD81 | CD229 | CD28 | CyIgκ | CyIgλ |

A further aspect of the invention relates to a diagnostic kit for detecting MRD, in particular BCP-ALL MRD, CLL MRD or MM/PCD MRD comprising one or more of the reagent compositions described herein above, optionally together with instructions for use, buffer, and/or control samples (see: Kalina et al. Leukemia 2012: 26: 1986-2010). In one embodiment, there is provided a BCP-ALL kit comprising one or more reagent compositions of Table 1. In another embodiment, there is provided a CLL kit comprising one or more reagent compositions of Table 2. In still a further embodiment, there is provided a PCD kit comprising one or more reagent compositions of Table 3.

The invention also relates to a method for flow cytometric detection of MRD, comprising the steps of providing a biological sample from a human subject and contacting at least a portion (aliquot) of the sample with a reagent composition provided herein. Any type of sample known or suspected to contain leukocytes may be used directly, or after lysing non-nucleated red cells, or after density centrifugation, or after cell sorting procedures. For example, the sample is peripheral blood, bone marrow, tissue sample such as lymph nodes, adenoid, spleen, or liver, or other type of body fluid such as cerebrospinal fluid, vitreous fluid, synovial fluid, pleural effusions or ascites. Peripheral blood or bone marrow is preferred.

Provided is a multi-color flow cytometric method for detecting minimal residual disease (MRD) in a biological sample comprising cells, preferably B-lineage cells (B-cell precursors, B-lymphocytes, and plasma cells), comprising the steps of:
(i) staining the sample with a reagent composition according to the invention,
(ii) subjecting the sample to flow cytometry; (iii) gating on cells for expression of the selected markers detected by the antibodies present in the reagent composition;
(iv) distinguishing between normal and malignant cells, based on the expression profile of the multiple markers.

Preferably, the analysis in step (iv) involves multivariate analysis, preferably principal component analysis (PCA), wherein each marker has added value in the distinction process via the principal component analysis. Advantageously, using automated population separation—APS view—is used employing for example Infinicyt software, or multidimensional scaling (MDS) analysis.

PCA is a mathematical procedure that uses an orthogonal transformation to convert a set of observations of possibly correlated variables into a set of values of uncorrelated variables called principal components. The number of principal components is less than or equal to the number of original variables. This transformation is defined in such a way that the first principal component has as high a variance as possible (that is, accounts for as much of the variability in the data as possible), and each succeeding component in turn has the highest variance possible under the constraint that it be orthogonal to (uncorrelated with) the preceding components. Principal components are guaranteed to be independent only if the data set is jointly normally distributed. PCA is sensitive to the relative scaling of the original variables. Depending on the field of application, it is also named the discrete Karhunen-Loève transform (KLT), the Hotelling transform or proper orthogonal decomposition (POD). Alternatively to PCA, MDS or any other type of well-established multivariate analysis, can be used (see: Pedreira et al. Trends Biotechnol 2013).

Figure 1:
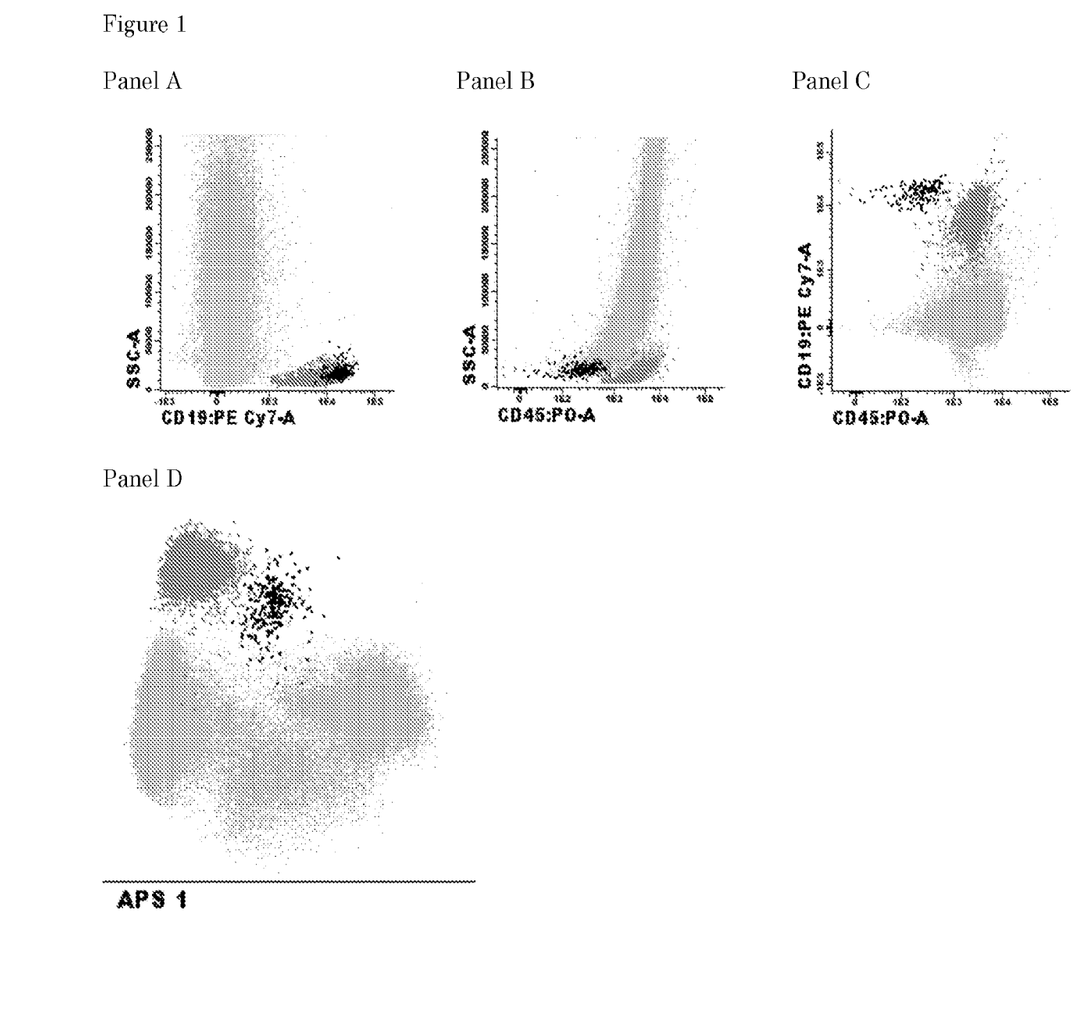
FIG. 1. Typical example of how to use the CD19 and CD45 identification markers in combination with SSC (Panel A to C) for the distinction between BCP cells and other nucleated cells in a bone marrow sample from a BCP-ALL patient during therapy. In each plot, light grey events correspond to non-B cells in the sample, while dark grey events are mature B-cells and black events BCP cells. In the multivariate analysis representation (APS1) of principal component 1 vs. principal component 2 (Panel D), both mature B cells and BCP cells are clearly separated from all other events based on all informative parameters (e.g. CD19, CD45, SSC).
Figure 2:
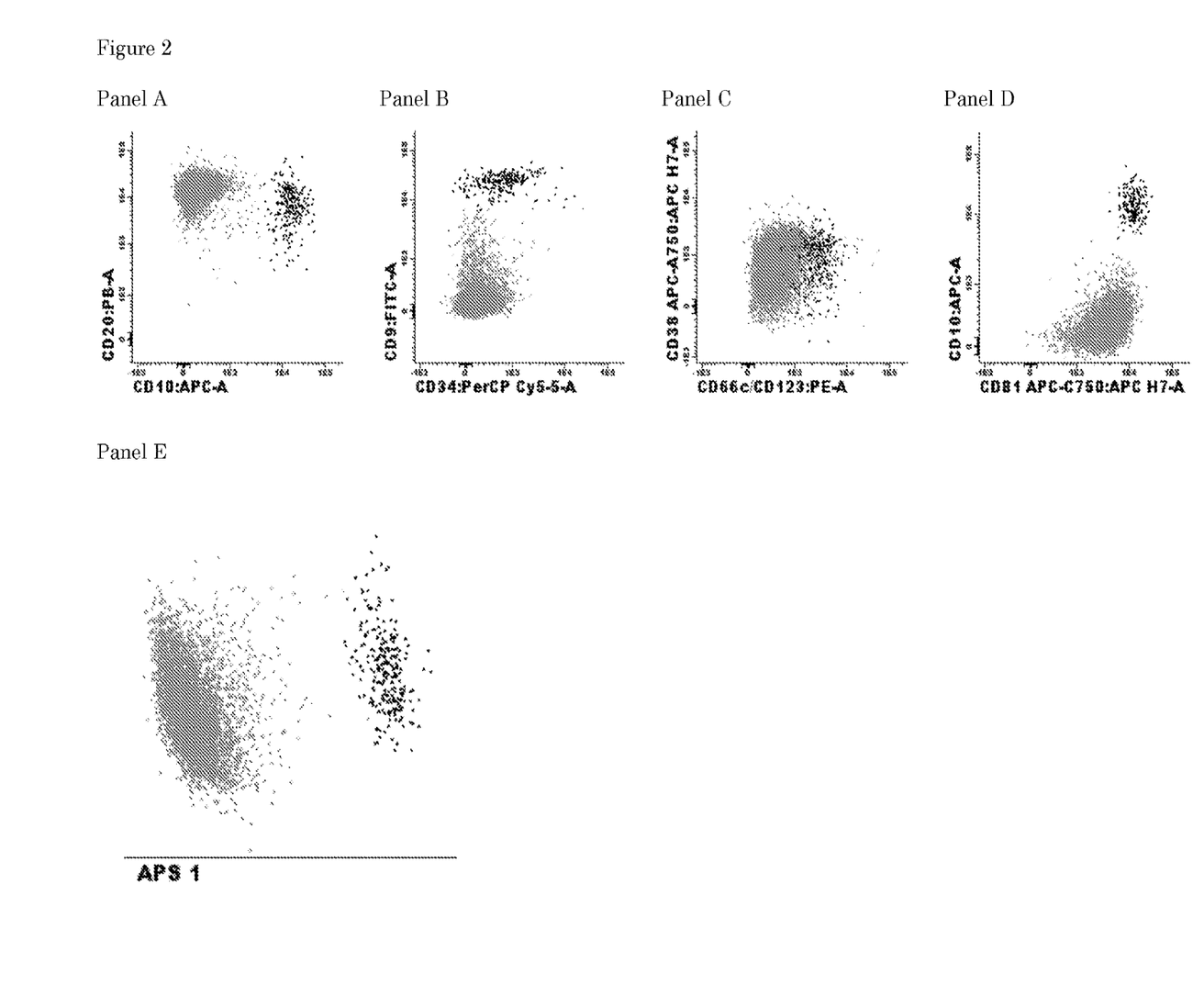

In one embodiment, there is provided is a multi-color flow cytometric method for detecting minimal residual disease (MRD) in a biological sample comprising lymphocytes, wherein MRD is BCP-ALL, comprising the steps of:
(i) staining the sample with a BCP-ALL reagent composition according to the invention, preferably a composition selected from any one of panels 1A, 1B or 1C;
(ii) subjecting the sample to flow cytometry; (iii) gating on mature B cells and BCP-cells for expression of the markers detected by the antibodies present in the reagent composition; (iv) distinction between normal and malignant BCP cells, based on the application of multiple markers, each having added value in the distinction process via the principal component analysis. See examples in Example 1 and FIGS. 1 and 2 for an exemplary analysis allowing for detection of MRD in BCP-ALL patients.

In another embodiment, there is provided is a multi-color flow cytometric method for detecting minimal residual disease (MRD) in a biological sample comprising lymphocytes, wherein MRD is CLL, comprising the steps of:

(i) staining the sample with a CLL reagent composition according to the invention, preferably a composition selected from any one of panels 2A, 2B or 2C;

(ii) subjecting the sample to flow cytometry; (iii) gating B-lymphocytes for expression of the markers detected by the antibodies present in the reagent composition; (iv) distinction between normal and malignant B cells, based on the application of multiple markers, each having added value in the distinction process via the principal component analysis.

Figure 3:
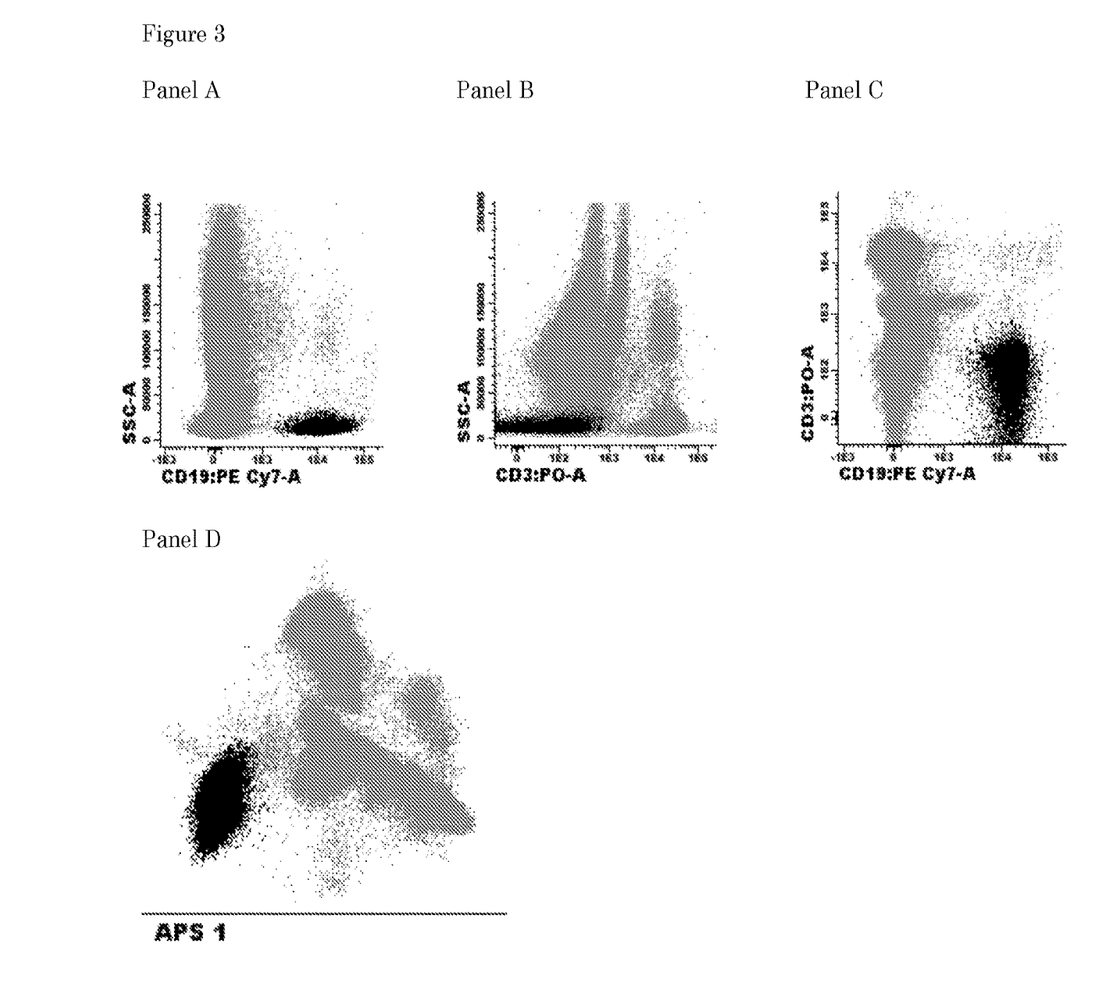
FIG. 3. —Illustrating example of how to use the CD19 and CD3 identification markers in combination with SSC (Panels A to C) for the distinction between mature B-cells and other nucleated cells in a peripheral blood sample from a CLL patient. In each plot, grey events correspond to non-B-cells in the sample, while black events are total peripheral blood B-cells. In the multivariate analysis representation (APS1) of principal component 1 vs. principal component 2 (Panel D), B-cells are clearly separated from all other events based on all informative parameters (e.g. CD19, CD3, SSC).
Figure 4:
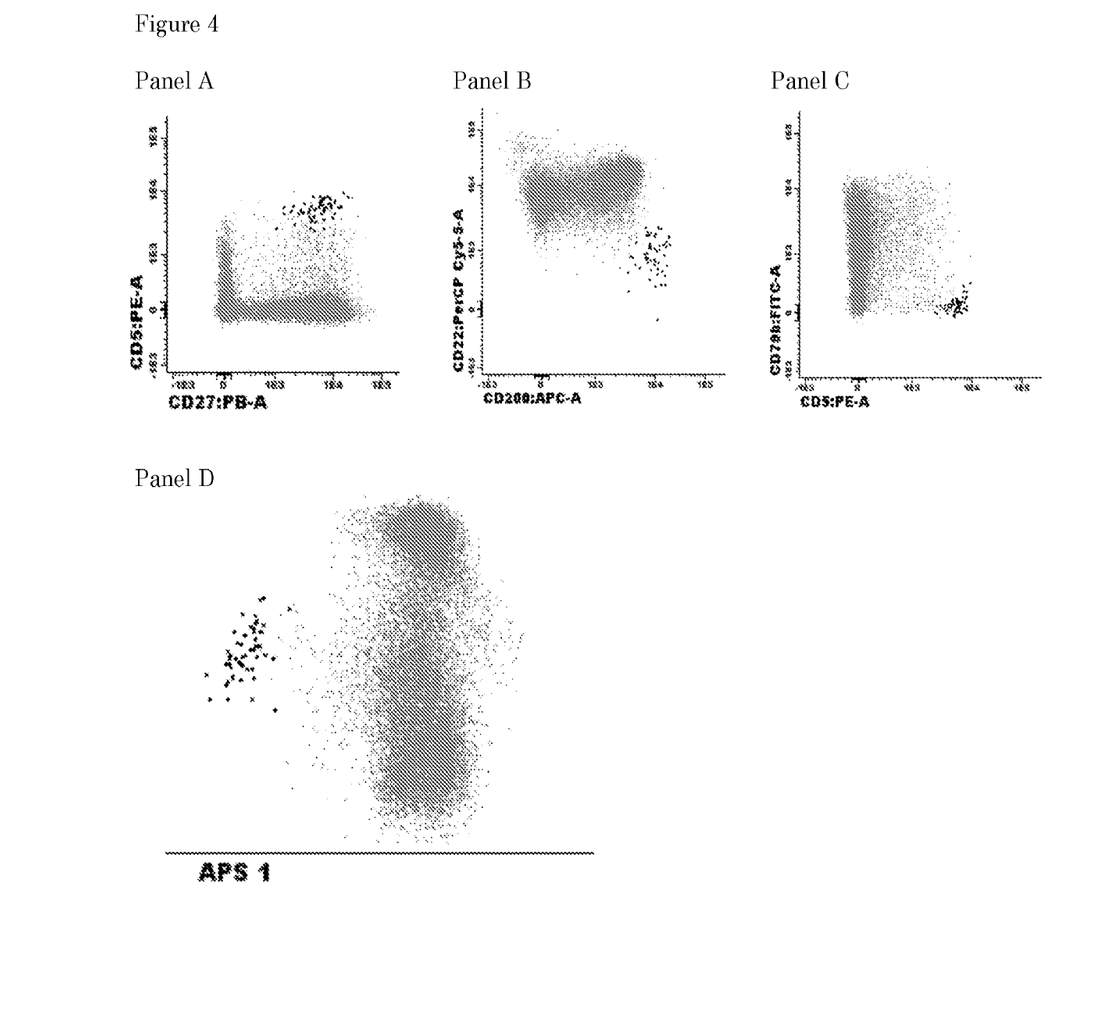

See examples in Example 2 and FIGS. 3 and 4 for an exemplary analysis allowing for detection of MRD in CLL patients.

In yet another embodiment, there is provided is a multi-color flow cytometric method for detecting minimal residual disease (MRD) in a biological sample comprising lymphocytes, wherein MRD is MM/PCD, comprising the steps of:

(i) staining the sample with a MM/PCD reagent composition according to the invention, preferably a composition selected from any one of panels 3A, 3B or 3C;

(ii) subjecting the sample to flow cytometry; (iii) gating plasma cells for expression of the markers detected by the antibodies present in the reagent composition; (iv)

distinction between normal and malignant plasma cells, based on the application of multiple markers, each having added value in the distinction process via the principal component analysis.

Figure 5:
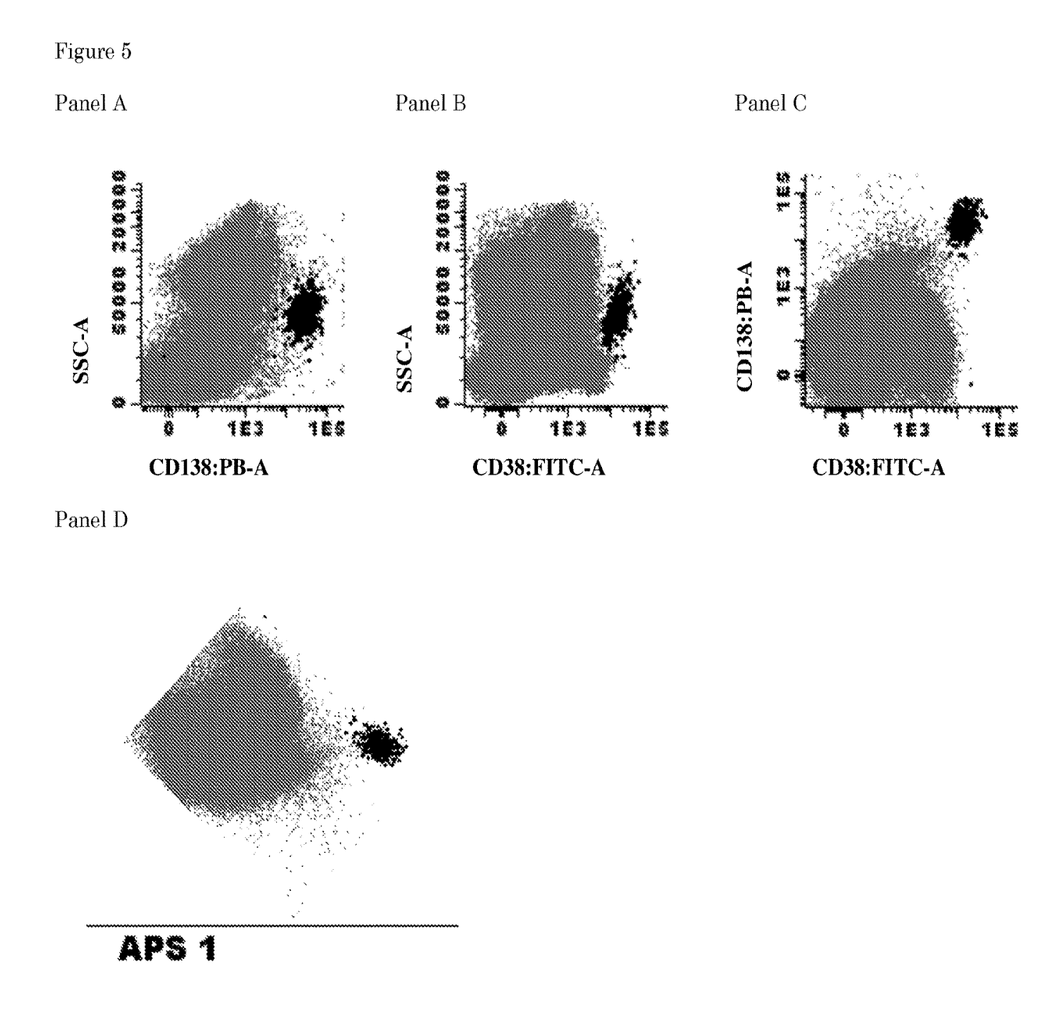
FIG. 5. —Illustrating example of how to use the CD38 and CD138 identification markers in combination with SSC (Panel A to C) for the distinction between plasma cells and other nucleated cells in a bone marrow sample of an MM patient after therapy. In each plot, grey dots correspond to non-plasma cells in the sample, while black dots are total bone marrow plasma cells. In the multivariate analysis representation (APS1) of principal component 1 vs. principal component 2 (Panel D), plasma cells (black dots) are clearly separated from all other events (grey dots) based on all informative parameters (e.g. CD138, CD38, SSC).
Figure 6:
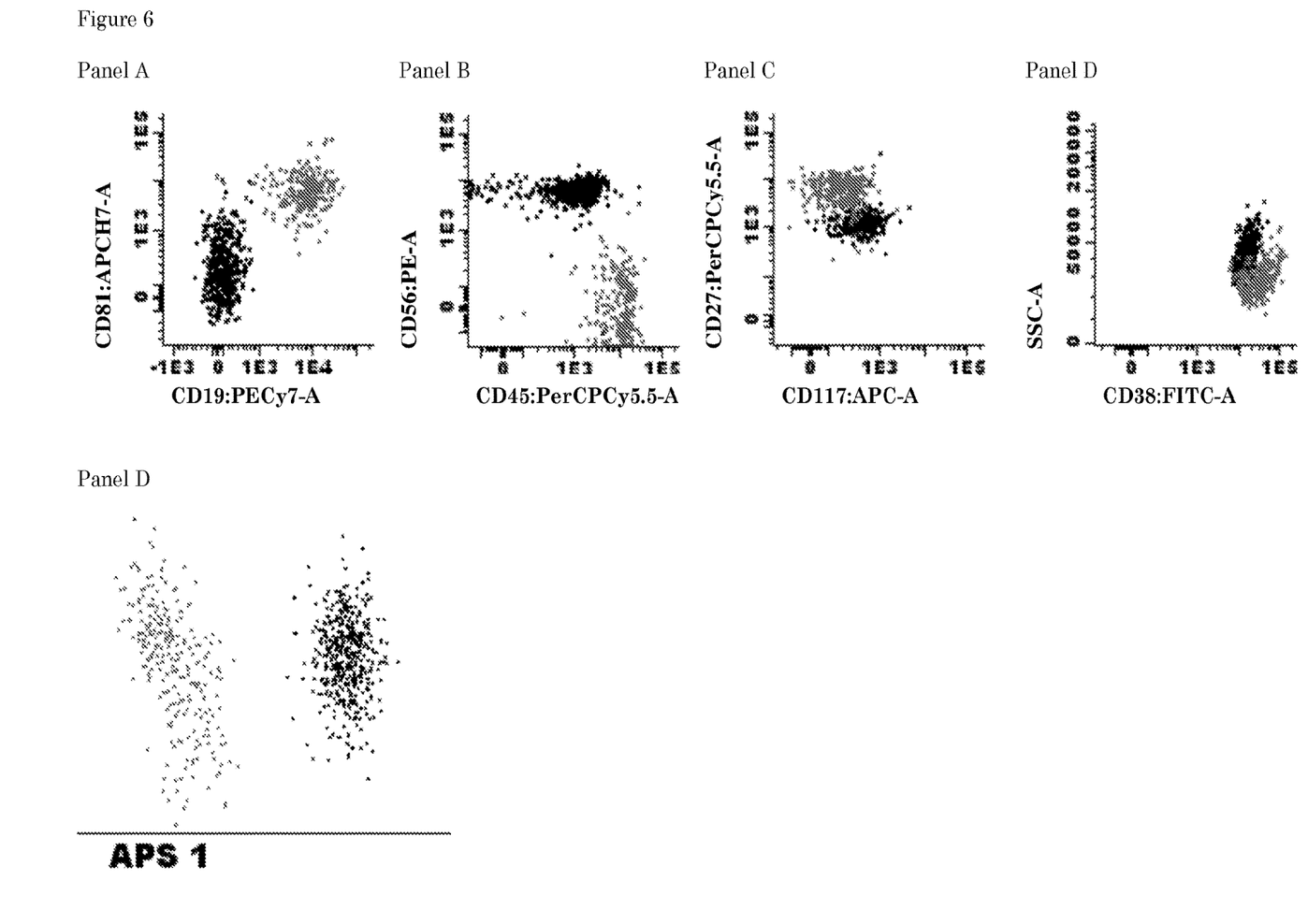

See examples in Example 3 and FIGS. 5 and 6 for an exemplary analysis allowing for detection of MRD in MM/PCD patients.

LEGEND TO THE FIGURES

FIG. 2. —Illustrating example of how to use immunophenotypic characterization markers CD10, CD20, CD34, CD66c/CD123, and CD38 in combination with SSC for the distinction between BCP-ALL cells and normal residual B-cells in a bone marrow sample from a BCP-ALL patient during therapy (Panels A to D). Only bone marrow B-cells are displayed, after gated/selected as described in FIG. 1. In each plot, black dots correspond to BCP-ALL cells in the sample, while grey dots are normal B-cells. Compared to normal B-cells, BCP-ALL cells show overexpression of CD81 (Panel D), CD10 (Panels A and D), and CD66c/CD123 (Panel C). In the APS1 (principal component 1 versus principal component 2) representation based on all immunophenotypic markers and scatter characteristics evaluated (Panel E), normal residual B-cells (grey) are clearly discriminated from BCP-ALL cells (black).

FIG. 4. —Illustrating example of how to use immunophenotypic characterization markers CD27, CD5, CD22, CD200 and CD79b (panels A to C) for the distinction between CLL cells and normal mature B-cells in a peripheral blood sample from a CLL patient. Only peripheral blood B-cells are displayed, after gated/selected as described in FIG. 3. In each plot, black dots correspond to CLL cells in the sample, while grey dots are normal peripheral blood B-cells. Compared to normal B-cells, CLL cells show underexpression of CD22 (Panel B) and CD79b (Panel C) together with overexpression of CD200 (Panel B) and CD5 (Panels A and C). In the APS1 (principal component 1 vs. principal component 2) representation based on all immunophenotypic markers and scatter characteristics evaluated (Panel D), CLL cells are clearly discriminated from normal B-cells, while this degree of discrimination could not be achieved based on individual markers.

FIG. 6. —Illustrating example of how to use immunophenotypic characterization markers CD81, CD19, CD45, CD56, CD27, CD117 and CD38, in combination with SSC (Panels A to D) for the distinction between myeloma/malignant plasma cells and normal residual plasma cells in a bone marrow sample of an MM patient after therapy. Only bone marrow plasma cells are displayed, after gated/selected as described in FIG. 5. In each plot, black dots correspond to myeloma/clonal plasma cells in the sample, while grey dots are normal residual bone marrow plasma cells. Compared to normal plasma cells, myeloma/clonal plasma cells show underexpression of CD81, CD19, CD45, CD27 and CD38 together with higher SSC and overexpression of CD56 and CD117. In the APS1 (principal component 1 vs. principal component 2) representation (Panel E) based on all immunophenotypic markers and scatter characteristics evaluated normal residual plasma cells (grey dots) are clearly discriminated from myeloma/malignant plasma cells (black dots), while this degree of discrimination could not be achieved based on individual markers.

EXPERIMENTAL SECTION

The power of the EuroFlow approach disclosed herein is based on the combination of sets of markers and the usage of multivariate analyses for both the identification of normal cells (e.g. normal precursor B-cells, normal B-lymphocytes and normal plasma cells) and the distinction between normal/reactive cells vs. clonal/malignant cells. For this purpose, a powerful multivariate analysis of the contribution of individual markers for inclusion and exclusion of each marker in the panel according to its contribution over all other markers in the combination. Such a strategy was used to evaluate the selected combinations of most discriminating markers in multiple sequential rounds of experimental testing. Because of this the final proposed antibody combinations became extremely strong when used in combination with the principal component analysis, specifically with the automated population separation (APS) tool of the Infinicyt software, so that the added (independent) value of each marker is used in a single step of analysis.

Herewith we provided the summary of the results of the extensive experimental studies for MRD detection in blood and bone marrow of patients with BCP-ALL (Example 1), CLL (Example 2) and Multiple Myeloma (Example 3).

In the Examples below, lists of markers are provided together with the most frequent phenotypic aberration of these markers in case of BCP-ALL, CLL, and MM/PCD. However, it should be noted that the real discrimination power between normal and malignant cells is based on combinations of markers in the corresponding n-dimensional space, as is clearly visible in the principle component analyses in the figures of Examples 1 to 3. In fact, minor differences of several markers add up to a larger difference in principle component analysis. Therefore the current invention is not about single marker studies for MRD detection, but about carefully selected sets of markers, that allow excellent discrimination between normal cells and their malignant counterparts, such as normal BCP cells vs. BCP-ALL blasts, normal B-lymphocytes vs. B-CLL cells, and normal plasma cells vs. MM/PCD plasma cells.

Example 1. Antibody Panels and Diagnostic Method for MRD Detection in BCP-ALL Patients Markers for Identification of Total B Cells and B-Cell Precursors in the Bone Marrow
List of relevant identification markers: CD19, CD45
How to use them: Pre-gating using the CD19 marker is essential for identifying a pure B-cell population. To focus on normal B-cell precursors (BCP), CD45-negativity or weak positivity can be used to discriminate BCP from CD45-positive mature B-cells. In case of CD19-directed therapies, CD19 might be replaced by CD22. These markers may be used in combination also with sideward light scatter (SSC) or forward light scatter (FSC) or both FSC and SSC to identify B-cells in peripheral blood or bone marrow or other types of samples (e.g. bone marrow, tissue biopsy, spinal fluid). Of note, other markers, like CD10, CD20, CD38 and CD34, which are used for discriminating BCP-ALL cells from normal BCP cells (see below), may also contribute to the gating of the total BCP cell population (e.g. CD34+, CD10+, CD20− to dim, CD38+).

Markers for Distinguishing Normal vs. Malignant B-Cell Precursor Cells
List of Markers and Most Frequent Phenotypic Aberration:
CD38: underexpressed in BCP-ALL/malignant vs. normal B-cell precursor cells
CD10: over- or underexpressed in BCP-ALL/malignant B-cell precursor cells
CD45: underexpressed (usually negative) in BCP-ALL/malignant vs. normal B-cell precursor cells
CD20: under- or overexpressed in BCP-ALL/malignant vs. normal B-cell precursor cells
CD81: over- or underexpressed in BCP-ALL/malignant vs. normal B-cell precursor cells
CD66c: overexpressed in BCP-ALL/malignant vs. normal B-cell precursor cells (particularly BCR-ABL positive ALL; generally negative in TEL-AML1-positive or MLL-AF4-positive ALL)
CD123: overexpressed in BCP-ALL/malignant vs. normal B-cell precursor cells (particularly in hyperdiploid ALL)
CD304: overexpressed in BCP-ALL/malignant vs. normal B-cell precursor cells
CD73: overexpressed in BCP-ALL/malignant vs. normal B-cell precursor cells
CD34: under- or overexpressed in BCP-ALL/malignant vs. normal B-cell precursor cells
SSC: increased or decreased intensity in BCP-ALL/malignant vs. normal B-cell precursor cells.
FSC: increased or decreased intensity in BCP-ALL/malignant vs. normal B-cell precursor cells.

Example 2. Antibody Panels and Diagnostic Method for MRD Detection in CLL Patients Markers for Identification of Total B-Cells in Peripheral Blood and Bone Marrow:
List of identification markers: CD19, CD3 (exclusion marker)
How to use them: Pre-gating using this marker combination is essential for identifying a pure B-cell population, and removing T-cell/B-cell doublets. These markers may be used in combination also with sideward light scatter (SSC) or forward light scatter (FSC) or both FSC and SSC to identify B-cells in peripheral blood or bone marrow or other types of samples (e.g. tissue biopsy, spinal fluid). For a more refined gating with better enrichment of CLL cells, both CD5 and CD27 may be used.

Markers for Distinguishing Normal B-Cells from CLL Cells:
List of Markers and Most Frequent Phenotypic Aberration:
CD27: positive on CLL cells and a small fraction of normal B-cells
CD5: positive on CLL cells and a small fraction of normal B-cells
CD79b: underexpressed on CLL cells as compared to normal transitional and mature B-lymphocytes
CD22: underexpressed on CLL cells as compared to normal transitional and mature B-lymphocytes
CD20: underexpressed on CLL cells as compared to normal transitional and mature B-lymphocytes
CD200: overexpressed on CLL cells as compared to normal transitional and mature B-lymphocytes
ROR1: overexpressed on CLL cells as compared to normal transitional and mature B-lymphocytes
CD43: overexpressed on CLL cells as compared to normal transitional and mature B-lymphocytes
CD81: underexpressed on CLL cells as compared to B-cell precursors and both transitional and mature B-lymphocytes
CD38: underexpressed on CLL cells as compared to B-cell precursors Example 3. Antibody Panels and Diagnostic Method for MRD Detection in MM/PCD Patients Markers for Identification of Total Plasma Cells in the Bone Marrow:
List of identification markers: CD38, CD138 and CD229
How to use them: Any combination of the three markers in any fluorochrome position works; also it is possible to use any combinations of two of the three markers or in a subset of cases (not all) even one of the three markers alone. Preferable combinations are order as follows: 1) CD138/CD38/CD229; 2) CD138/CD38, 3) CD138/CD229; 4) CD38/CD229; 5) CD138; 6) CD38); 7) CD229. Note that any of these markers individually and in combination may be used in combination also with sideward light scatter (SSC) or forward light scatter (FSC) or both FSC and SSC to identify plasma cells in the bone marrow or other types of samples (e.g. peripheral blood, tissue biopsy, spinal fluid).

Markers for Distinguishing Normal vs Clonal/Malignant Plasma Cells:

List of Markers and Most Frequent Phenotypic Aberration:

CD38: underexpressed in malignant plasma cells compared to normal plasma cells

CD27: underexpressed in malignant plasma cells compared to normal plasma cells

CD45: underexpressed in malignant plasma cells compared to normal plasma cells

CD19: underexpressed (usually negative) in malignant plasma cells compared to normal plasma cells CD81: underexpressed in malignant plasma cells compared to normal plasma cells CD56: overexpressed in malignant plasma cells compared to normal plasma cells CD28: overexpressed in malignant plasma cells compared to normal plasma cells CD117: overexpressed in malignant plasma cells compared to normal plasma cells CyIgk and CyIglambda: expression restricted to either one or the other Ig light chains in malignant plasma cells while showing a balanced distribution (CyIgk/CyIglambda ratio in normal plasma cells usually ranging between ratios 3 and 0.5).

SSC: increased or decreased intensity in malignant plasma cells compared to normal plasma cells.

FSC: increased or decreased intensity in malignant plasma cells compared to normal plasma cells.

The invention claimed is:

1. A diagnostic kit, comprising two 8-color reagent compositions for flow cytometric detection of multiple myeloma (MM) or plasma cell disorders (PCD) in a human subject, the 8-color reagent compositions comprising distinct panels fluorochrome-conjugated antibodies directed against the following combinations of markers:
    (i) CD138, CD27, CD38, CD56, CD45, CD19, CD117 and CD81; and
    (ii) CD138, CD27, CD38, CD56, CD45, CD19, CyIgκ and CyIgλ.

2. The kit according to claim 1, wherein for each of the panels the following combination of fluorochromes is used: (1) pacific blue (PacB), brilliant violet 421 (BV421) or Horizon V450, (2) pacific orange (PacO), Horizon V500 (HV500), BV510, Khrome orange (KO) or OO515, (3) fluorescein isothiocyanate (FITC) or Alexa488, (4) phycoerythrin (PE), (5) peridinin chlorophyl protein/cyanine 5.5 (PerCP-Cy5.5), PerCP or PE-TexasRed, (6) phycoerythrin/cyanine7 (PE-Cy7), (7) allophycocyanine (APC) or Alexa647, and (8) allophycocyanine/hilite 7 (APC-H7), APC-Cy7, Alexa680, APC-A750, APC-C750 or Alexa700.

3. The kit according to claim 1, wherein the antibody against CD138 is conjugated to PacB, BV421 or HV450; the antibody against CD27 is conjugated to HV500 or PacO; the antibody against CD38 to FITC; the antibody against CD56 to PE; the antibody against CD45 against PerCPCy5.5; the antibody against CD19 to PECy7; the antibody against CD117 and the antibody against CyIgκ to APC; and the antibody against CD81 and the antibody against CyIgλ to APCH7, APCA750 or APCC750.

4. A 10-color reagent composition for flow cytometric detection of multiple myeloma (MM) or plasma cell disorders (PCD) in a human subject comprising distinct fluorochrome-conjugated antibodies directed against the markers CD138, CD27, CD38, CD56, CD45, CD19, CD117, CD81, CyIgκ and CyIgλ.

5. A 12-color reagent composition for flow cytometric detection of multiple myeloma (MM) or plasma cell disorders (PCD) in a human subject comprising distinct fluorochrome-conjugated antibodies directed against the markers CD138, CD27, CD38, CD56, CD45, CD19, CD117, CD81, CyIgκ, CyIgλ, CD229 and CD28.

6. A multi-color flow cytometric method for detecting multiple myeloma (MM) or plasma cell disorders (PCD) in a biological sample comprising cells, preferably lymphocytes, comprising the steps of:
    (i) staining the sample with the two 8-color reagent compositions of any one of claims 1-3, or the 10-color reagent composition of according to claim 4, or the 12-color reagent composition of claim 5;
    (ii) subjecting the sample to flow cytometry;
    (iii) gating on cells for expression of the selected markers detected by the antibodies present in the reagent compositions; and
    (iv) distinguishing between normal and malignant cells, based on the expression profile of the multiple markers, wherein CD38, CD27, CD45, CD19 and CD81 are underexpressed in malignant cells compared to normal cells, wherein CD56, CD28 and CD117 are overexpressed in malignant cells compared to normal cells, and wherein expression of CyIgκ and CyIgλ is restricted to either one or the other Ig light chains in malignant cells.

7. The method according to claim 6, wherein step (iv) involves multivariate analysis, preferably principal component analysis (PCA).

8. The method according to claim 6, wherein the biological sample is a peripheral blood sample or a bone marrow sample.

9. The method according to claim 7, wherein the biological sample is a peripheral blood sample or a bone marrow sample.

* * * * *